United States Patent [19]

Edelman et al.

[11] Patent Number: 5,005,180
[45] Date of Patent: Apr. 2, 1991

[54] LASER CATHETER SYSTEM

[75] Inventors: William Edelman, Seal Beach; Dennis Constantinou, Corona Del Mar; Miles Stefanovski, Santa Ana; Yuh L. Jan, El Toro; Theodore S. Fahlen, San Jose; Ronald L. Hansen, San Jose; Kenneth J. Kramasz, San Jose, all of Calif.

[73] Assignee: Schneider (USA) Inc., Minneapolis, Minn.

[21] Appl. No.: 402,135

[22] Filed: Sep. 1, 1989

[51] Int. Cl.$^5$ .............................................. H01S 3/22
[52] U.S. Cl. ........................................ 372/57; 372/59; 372/6
[58] Field of Search ........................... 372/57, 6, 59, 70

[56] References Cited

U.S. PATENT DOCUMENTS

| | | |
|---|---|---|
| 3,408,593 | 4/1964 | Hurwitz, Jr. . |
| 4,143,337 | 3/1979 | Beaulieu . |
| 4,207,874 | 6/1980 | Choy . |
| 4,240,044 | 12/1980 | Fahlen et al. . |
| 4,393,505 | 7/1983 | Fahlen ................. 372/57 |
| 4,504,114 | 3/1985 | Arrington . |
| 4,601,039 | 7/1986 | Sze . |
| 4,641,912 | 2/1987 | Goldenberg . |
| 4,681,104 | 7/1987 | Edelman . |
| 4,686,979 | 8/1987 | Gruen . |
| 4,732,448 | 3/1988 | Goldenberg . |
| 4,862,886 | 9/1989 | Clarke et al. ............ 372/57 |

OTHER PUBLICATIONS

Gibson et al., "A Transversely Excited Multiatmosphere CO2 Wavegide Laser", Applied Physics Letters, vol. 31, No. 3, Aug. 1977, pp. 176–178.
Jane et al., "Ultraviolet-Laser Ablation of Skin and Other Tissue", Tech. Digest Conference on Lasers & Electrooptics, FL1, 1984.
W. S. Grundfest et al., "Effect of Excimer Laser Irradiation on Human Atherosclerotic Aorta: Amelioration of Laser-Induced Thermal Damage", Tech. Digest Conference on Lasers & Electrooptics, FL2, 1984.
Sze, "Inductively Stabilized Long-Pulsed Excimer Lasers", Topical Meeting on Excimer Lasers, Incline Village, Nev., Jan. 10–12, pp. MB6-1 through MB6-4, 1983.

(List continued on next page.)

Primary Examiner—Léon Scott, Jr.
Attorney, Agent, or Firm—Knobbe, Martens, Olson & Bear

[57] ABSTRACT

A fiber optic device for remote delivery of intense ultraviolet optical signals comprising an excimer laser source and an optical fiber. The output of the pulsed, transverse discharge, high pressure laser source is coupled to an articulating reflection mechanism which directs the pulsed laser output to an input end of the optical fiber. The optical fiber serves to transmit the light from the laser source to a remote location or target. The excimer laser further comprises a segmented first elongated laser electrode and a coextensive second laser electrode which is substantially solid. The discharge is stabilized by inductors connected to each segment of the first electrode and further by preionization electrodes located adjacent and coextensive with the second electrode. The preionization electrodes comprise a central conductor surrounded by a dielectric sleeve. The laser further comprises a closed gas system for the lasing medium gas. The gas system comprises a circulating blower, a heat exchanger and a cryogenic trap. The optical fiber comprises a central core having a substantially constant index of refraction and a cladding having an index of refraction which varies as the radius of the cladding. Thus, the invention advantageously permits high intensity ultraviolet light to be generated over extended periods of time utilizing a sealed laser and furthermore delivers the high intensity ultraviolet light to a remote location through an optical fiber with minimal damage to the fiber. The system is particularly well suited for application as a percutaneously introduced laser angioplasty system for removal of vascular obstructions.

15 Claims, 7 Drawing Sheets

OTHER PUBLICATIONS

Boucher, et al., "Ultraviolet (UV) Transmission of Plastic Clad Silica (PCS) Fibers: Characteristics, Measurements, Methods and Production".

Itoh, et al., "High-Power KrF Laser Transmission Through Optical Fibers and Its Application to the Triggering of Gas Switches".

E. A. Nevis, "Alteration of the Transmission Characteristics of Fused Silica Optical Fibers by Pulsed Ultraviolet Radiation", SPIE, vol. 540, Southwest Conference on Optics (1985).

S. W. Allison, et al., "Pulsed Laser Damage to Optical Fibers", *Applied Physics*, vol. 24, No. 19, Oct. 1985.

Kan-Ich Fujii et al., "A Resistively Stabilized XeCl Laser Operating at 200 Hz", IEEE Journal of Quantum Electronics, vol. QE-17, No. 8, Aug. 1981, pp. 1315–1317.

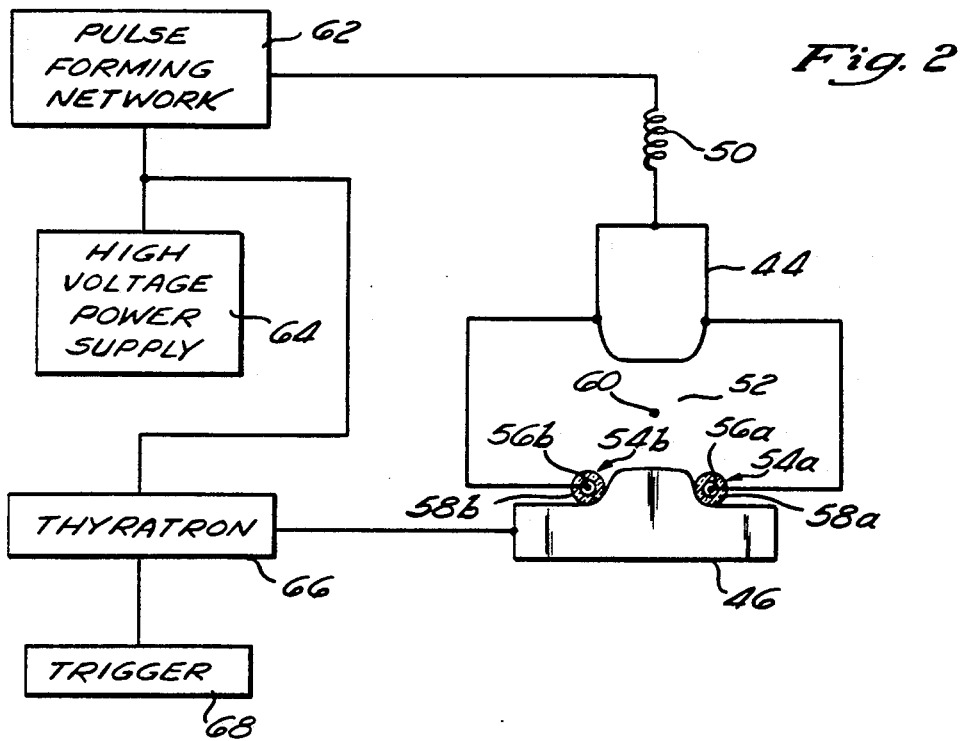
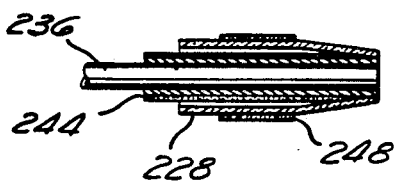
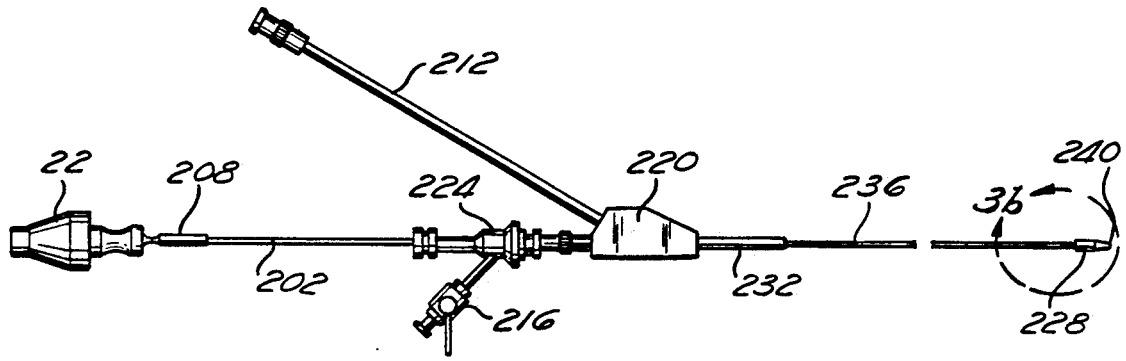

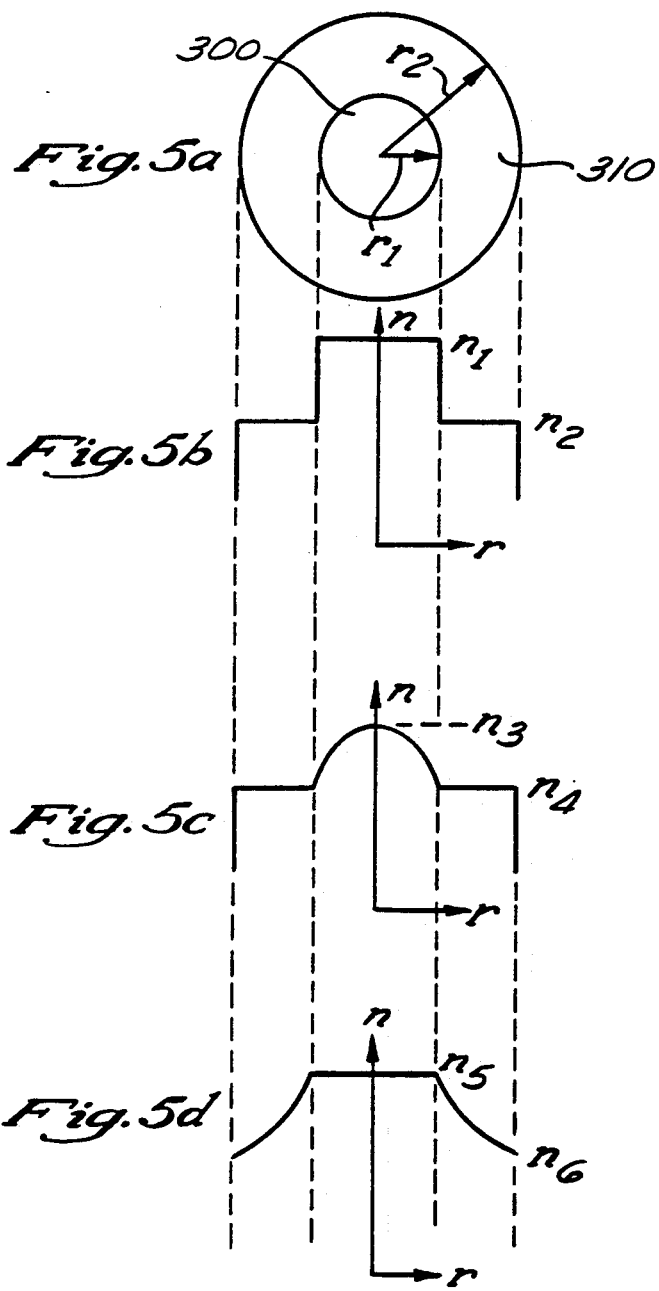
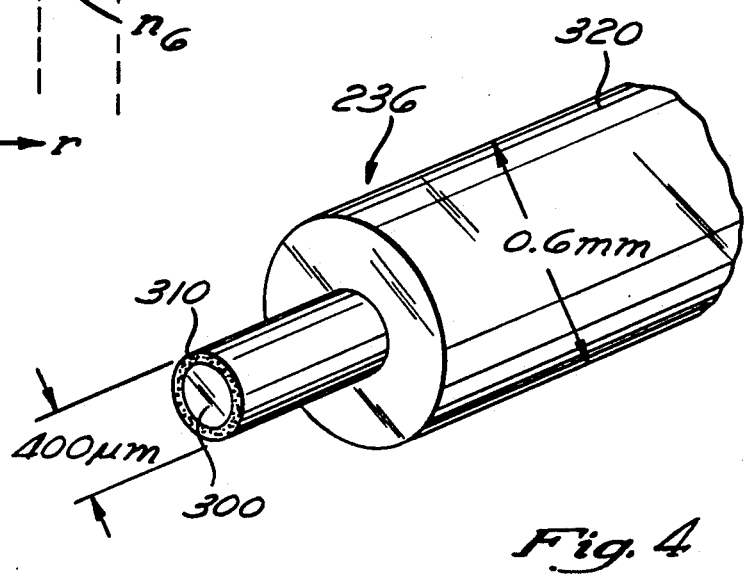

LASER CATHETER SYSTEM

FIELD OF THE INVENTION

The invention relates generally to the art of producing optical signals and transmitting the signals via fiber optics, and particularly to the delivery of light to biotic material for medical treatment. Among other medical applications, the invention may be used to apply optical energy to the lumen of a blood vessel for the purpose of removing obstructions from the lumen or otherwise structurally modifying the vessel utilizing the optical energy.

BACKGROUND OF THE INVENTION

Arteriosclerosis, a chronic disease characterized by abnormal thickening and hardening of the arterial walls, is a leading cause of death in the United States. Arteriosclerosis begins when fatty streaks form within the arteries along the arterial walls. Over the years, these streaks enlarge, form connective tissue and calcium, and often cause blockage of blood flow through the arteries. If these blockages, called plaques, occur in the coronary arteries, they may cause a heart attack. Blockages in the arteries of the head and neck may cause strokes and blockages in the arteries of the legs may cause gangrene.

The most commonly used remedy for arteriosclerosis is bypass surgery, a major operation in which veins are taken from the patient's limbs and grafted onto the diseased artery to carry blood around the obstruction in the artery. Bypass surgery is an expense and dangerous procedure which is often less than 100% effective.

An alternative to bypass surgery is a recently developed technique called balloon angioplasty. Balloon angioplasty requires that a catheter be inserted into an artery of the arm or leg and pushed through the arterial passage until it reaches the partially blocked area of the artery. A tiny balloon on the tip of the catheter is then inflated to deform the plaque deposits, thus widening the arterial channel and facilitating the flow of blood through the vessel. Balloon angioplasty is not an appropriate treatment for every case of arteriosclerosis. In the cases not treatable by balloon angioplasty techniques, the arteries are either too clogged to permit insertion of the catheter into the region of the blockage, or the calcified fat deposits are too hard to be deformed. Even in the cases where balloon angioplasty is applicable, the remedy may not last for longer than a year before the blockage reoccurs.

A promising new development for the treatment of arteriosclerosis is a procedure called laser angioplasty. This procedure utilizes a catheter which is inserted into the artery and advanced to the site of the obstruction. An optical fiber is inserted through the catheter and positioned at the obstruction. The optical fiber is attached on one end to a laser. The laser energy which is guided through the fiber exits at the distal end of the fiber and is absorbed by the obstruction. Through a variety of mechanisms, depending in part on the wavelength of the laser energy, the obstruction is destroyed by the absorption of the laser energy and thus removed from the artery. The major advantage of laser angioplasty over balloon angioplasty is that the obstruction is removed from the artery. Furthermore, in contrast to balloon angioplasty, laser angioplasty may be used where there is a complete blockage of the artery.

Presently, three types of lasers, $CO_2$, Nd:YAG, and argon ion, are commonly used in medical applications. The choice as to which laser to use for a particular application depends on a number of factors, as the effect of laser light on tissue varies with the wavelength, intensity, and mode of delivery of the laser light. In general, the mode of delivery for a laser is either continuous output or output in the form of a series of pulses.

$CO_2$ lasers emit light in the far infrared, wavelength of 10,600 nm, and are typically used in the continuous mode to ablate tissue. Since the laser energy is readily absorbed by the tissue water, it penetrates the tissue to a depth of only 50 $\mu$m to 100 $\mu$m. If the absorbed far infrared light energy is sufficiently intense, the water component within the cell may vaporize into steam and heat the surrounding organic material. This photothermal ablation of tissue is the common mechanism of tissue vaporization by conventional medical lasers.

Nd:YAG lasers emit light at wavelengths of 1060 nm and 1318 nm. Operated in the continuous mode, Nd:YAG laser energy penetrates tissue more deeply than $CO_2$ laser energy and is absorbed largely by proteins. As larger volumes of tissue are heated with the same amount of energy, Nd:YAG laser energy tends to produce tissue necrosis and coagulation before it produces significant photothermal ablation.

Argon gas lasers emit a blue-green light at wavelengths of 488 nm and 514.5 nm. The argon laser energy is most strongly absorbed by pigmented material, particularly hemoglobin and myoglobin. Therefore, its penetration depth varies with the color of the target tissue. Argon gas laser energy is commonly delivered in the continuous mode and modifies or destroys tissue by the photothermal ablation mechanism described previously in connection with $CO_2$ laser energy.

The $CO_2$, Nd:YAG, and Argon lasers have two features which are significant limitations for application to laser angioplasty. First, all of these lasers produce their effect by thermal effects which can cause thermal injury to surrounding healthy tissue. Second, none of these lasers are capable of ablating densely calcified tissue. Additionally, there are no sufficiently flexible fiber optics which are capable of transmitting $CO_2$ laser energy, and the fiber optics for transmission of the argon and Nd:YAG laser energy tend to melt when intravascular debris accumulates on the tip of the fiber.

The limitations of the $CO_2$, Nd:YAG, and argon lasers for applications to laser angioplasty lead to a search for a laser having characteristics more suitable for the procedure. It was found that lasers emitting light in the ultraviolet (UV) region of the spectrum possess three important characteristics which are potentially advantageous for medical applications and particularly for laser angioplasty. First, UV light is intensely absorbed at the surface of living tissue. Second, UV light produces little or no thermal injury to living tissue and finally, it ablates densely calcified material. In contrast to the ablation produced by $CO_2$, Nd:YAG and argon lasers, ablation produced by UV laser energy has been found to: (1) produce an incision that conforms precisely to the laser beam configuration with no evidence of carbonization of surrounding tissue, (2) produce minimal thermal injury to surrounding tissue, and (3) preserve the tissue architecture. In addition, unlike the $CO_2$, Nd:YAG and argon lasers, ultraviolet lasers can cut through bone, opening possibilities for precise facial reconstruction. Additionally, ultraviolet lasers open possibilities for advanced ophthalmologic procedures such as radial keratotomy and delicate neurosurgical procedures.

The superior performance of ultraviolet photons is believed to be due in part to the mechanism of tissue interaction. Specifically, ultraviolet photons carry enough energy to break chemical bonds. As a result, the photons chemically dissociate the molecules comprising the tissue. The tissue is vaporized because the fragments of the molecular dissociation occupy a larger volume than the original material. This process, known as photochemical ablation, removes plaque from blood vessels with minimal generation of heat, and the heat that is produced is carried away by the ejected fragments. Greater precision is thought to occur with the photochemical ablation process because tissue is no longer destroyed by thermal energy. Alternatively, the exquisite precision observed with ultraviolet laser energy may result from the application of the laser energy in pulses having very short durations (10–300 nsec) and at frequencies ranging from ten hertz to several hundred hertz. Thus, the off time between pulses allows the tissue to cool before additional energy is deposited at the site.

Ultraviolet laser energy suitable for medical applications can be produced by a class of lasers called excimer lasers. The wavelength produced by the excimer lasers depends on the type of gas used for the lasing medium. For example, argon fluoride (ArF), krypton fluoride (KrF), xenon chloride (XeCl), and xenon fluoride (XeF) excimer lasers generate ultraviolet light having wavelengths of 194 nm, 248 nm, 308 nm, and 355 nm, respectively. All of these wavelengths are in the ultraviolet and possess advantageous properties for plaque removal. Thus, excimer lasers are currently the leading candidates for use in laser angioplasty applications.

Notwithstanding the clear advantages of ultraviolet laser energy for angioplasty applications, the technique has not been met with widespread acceptance for laser angioplasty because of two significant hardware limitations. First, the high peak power, defined as the pulse energy divided by the pulse width, and absorptive characteristics of the excimer laser energy within an optical fiber are difficult to control. This may result in damage to the fiber transmission system, leading to a short useful life for the fiber. Second, the laser gases are highly toxic and have, in the past, not been generally acceptable for use in the environment of a hospital or operating room.

Many of the deficiencies found in presently used $CO_2$, Nd:YAG, and argon laser based angioplasty systems could be overcome by use of the ultraviolet photon energy delivered by excimer lasers. Unfortunately, even though the advantages of excimer lasers for laser angioplasty are widely recognized, prior systems have been restricted to use in experimental settings because of limited lifetimes of the lasers and optical transport systems and the need to isolate the toxic excimer laser gases from the surrounding environment.

Accordingly, there is a need for a laser angioplasty system which utilizes excimer lasers and is capable of operating for extended time periods without interruptions. Additionally, the system should have provision for isolating the excimer laser medium gases from the hospital and operating room environments.

SUMMARY OF THE INVENTION

The present invention circumvents the problems of limited useful life and dangers of toxic gases and enables the delivery of energetic optical signals to remote locations. For example, the present invention may be incorporated into a device for performing advanced medical procedures including laser angioplasty.

The present invention is particularly appropriate for use in a new medical procedure in which an optical fiber may be used as a probe for delivery of ultraviolet light to the lumen of a blood vessel. It has been found that arteriosclerotic lesions which contain cholesterol can be reduced in size by directing high energy pulses of ultraviolet light onto the lesion. In this procedure, the optical fiber is threaded through the blood vessel to expose the lesions to the ultraviolet light. Cholesterol in the lesion selectively absorbs the ultraviolet light, thereby leading to a reduction in size of the lesion. Tests indicate that the ultraviolet light reduces the lesion without significant risk of damage to surrounding blood and healthy tissues. The present invention is thus particularly advantageous for use with this medical procedure, as it provides a convenient method for delivering high power pulses of ultraviolet energy to the lumen of blood vessels without radical surgery.

According to the present invention, there is disclosed, in a first embodiment, an apparatus for producing and transmitting energetic optical signals, characterized by: 1) an excimer laser for producing ultraviolet light, wherein the laser comprises: (a) a first elongated laser electrode having a plurality of segments, there being associated with each of the segments an individual inductive element through which each of the segments is connected to a common bus; (b) a second elongated laser electrode spaced apart from the first laser electrode, the second electrode positioned substantially parallel to the first laser electrode and substantially coextensive therewith, the space between the first and second laser electrodes forming a laser discharge gap; (c) a preionizer positioned adjacent to one of the first and second laser electrodes throughout the effective length of the one laser electrode, the preionizer comprising a conductive element within an insulating tube, the insulating tube proximate the one laser electrode and the conductor element in electrical connection with the other of the laser electrodes; (d) a housing for the first and second laser electrodes, the housing defining a cavity suitable for confining a gaseous laser medium, the housing cavity allowing exchange of the gaseous laser medium between the cavity and the laser discharge gap; (e) a pulse forming network for producing electrical pulses for application to the laser electrodes to generate an electrical discharge in the gaseous laser medium in the laser discharge gap; (f) a gas circulator for circulating the laser medium within the housing cavity; and (g) a trap through which the gaseous laser medium may be passed, the trap removing impurities from the gaseous medium; 2) an optical fiber having an input end and an output end, the input end receiving optical signals from the laser and guiding them through the fiber to the output end, the fiber further comprising a substantially rod shaped core material surrounded by a substantially tube shaped cladding material, the cladding material having an optical index of refraction which is less than or equal to the index of refraction of the core material at an interface between the core and the cladding, the index of refraction of the cladding material decreasing as the radial distance from the interface increases; and 3) a control system for monitoring and controlling the operation of the laser.

There is also disclosed, in a second embodiment of the invention, a method of treating a patient with a medical laser. The method is characterized by the steps of: 1) generating intense energetic optical pulses of light; 2) transmitting the pulses of light through an optical fiber having a cladding with a refractive index that varies along a radial dimension of the fiber; 3) positioning the fiber such that the signals are directed to a treatment site of the patient; and 4) utilizing the pulses to treat the patient at the treatment site. Typically, the pulses are at least a few tens of nanoseconds in length. In one embodiment, the generating step comprises generating intense energetic optical pulses of ultraviolet light. For some applications, the positioning step comprises guiding the fiber through a catheter. The catheter may further be inserted into a blood vessel. The method is often useful for nonthermally ablating atherosclerotic plaque.

There is also disclosed, in a third embodiment of the invention, an improved medical laser apparatus having an optical fiber for guiding intense optical signals to a remote location in a patient. The fiber has a core, for conducting the intense optical signals to the remote location, and a cladding, which has an index of refraction which is nonuniform along a radial dimension of the fiber. This configuration is useful for enhancing the optical power transmission through the core. Typically, the cladding surrounding the core has an index of refraction which is lower than the core. In a preferred embodiment, the wavelength of the intense optical signals is selected to ablate biotic material at the remote location in the patient. Preferably, the index of refraction varies as a function of the distance along the radial dimension. In many instances, the intense optical signals are generated by an excimer laser. One type of such excimer laser comprises a gas lasing medium of krypton and fluorine. Another type of such excimer laser comprises a gas lasing medium of xenon and chlorine. It is sometimes advantageous for the wavelength to be located in the ultraviolet region of the optical spectrum. For example, one particularly useful wavelength is on the order of about 250 nm. Another particularly useful wavelength is on the order of about 310 nm. It may also be advantageous for the signals to be in the form of pulses. For example, the pulses may have a duration on the order of approximately 75 ns and may be at a frequency of on the order of about 1,000 pulses/second or less. One embodiment of the invention further comprises a fluorine detector. In another embodiment, the invention may further comprise a computer control system. In yet another embodiment, the signals comprise a series of pulses, each of the pulses having a duration of at least a few tens of nanoseconds. In some applications of the invention, it is often advantageous to incorporate a catheter for guiding the optical fiber to the remote location. It may also be advantageous to select the wavelength such that biotic material is nonthermally ablated. It may be preferable for the signals to comprise a series of pulses, each of the pulses having an energy density on the order of at least about 100 millijoules/$cm^2$, and having a duration of at least a few tens of nanoseconds. Alternatively, the signals may comprise a series of pulses, each of the pulses having an energy density of at least several hundred millijoules/$cm^2$, and having a duration of at least a few tens of nanoseconds.

These and other features of the invention may be more fully understood through reference to the accompanying drawings.

BRIEF DESCRIPTION OF THE DRAWINGS

FIG. 3a is an illustration of the fiber optic catheter of the invention.

FIG. 3b is an enlargement of the distal end of the catheter shown in FIG. 3a.

FIG. 4 is a drawing of the structure of a typical optical fiber.

FIG. 5a is an end view of a typical optical fiber showing the core and the cladding of the fiber.

FIG. 5b is a plot of the indices of refraction of the core and cladding of a typical step index optical fiber.

FIG. 5c is a plot of the indices of refraction of the core and cladding of a typical graded-index core optical fiber.

FIG. 5d is a plot of the indices of refraction of the core and cladding of a typical graded-index cladding optical fiber.

FIG. 7 is a flowchart of the main software program for the computer control system.

DETAILED DESCRIPTION OF THE PREFERRED EMBODIMENT

Figure 1:
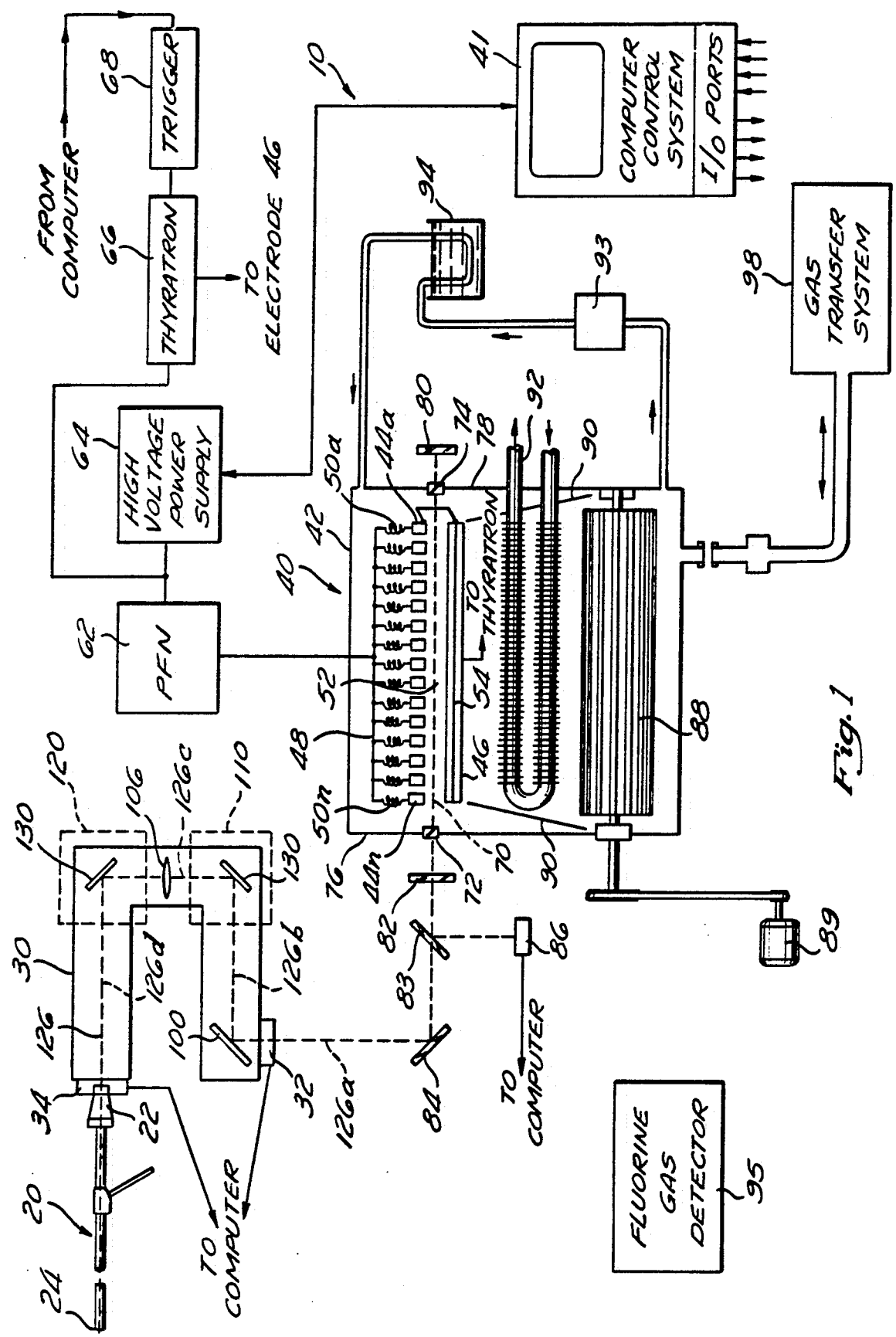
FIG. 1 is a block diagram of one embodiment of the invention.

As shown in FIG. 1, a laser angioplasty system 10 of the present invention comprises an optical fiber catheter 20 having an input end 22 and an output end 24. The catheter 20 is coupled to an articulating reflection mechanism 30 having an input shutter assembly 32 and an output interlock port 34. A laser source 40 is coupled to the articulating reflection mechanism 30 for supplying optical signals to the input shutter 32. The optical signals propagate through the articulating reflection mechanism 30 to the input end 22 of the catheter 20 wherein they are guided to the output end 24 of the catheter 20. A computer or microprocessor control system 41 coordinates the activities of the various components of the system, performs data storage and retrieval functions, and records system operation histories.

LASER LIGHT SOURCE

The laser 40 shown in FIG. 1 is suitable for producing high intensity light which is effective in removing cholesterol deposits from the inside walls of blood vessels while causing minimal damage to the healthy tissue surrounding the unwanted deposits. In one embodiment of the invention, the laser 40 comprises a high pressure, (greater than one atmosphere) transverse discharge excimer laser. In one embodiment, the excimer laser of choice is a krypton fluoride (KrF) laser which produces laser light at a wavelength of approximately 248 nm. The gas mixture for this embodiment comprises approximately 0.2% fluorine gas, approximately 3.85% krypton gas and approximately 95.95% neon gas. In another embodiment of the invention, the excimer laser of choice is a xenon chloride (XeCl) laser which produces laser light at a wavelength of approximately 308 nm. The gas mixture for this embodiment comprises approximately 2.5% xenon gas, approximately 0.1% hydrogen chloride (HCl) and approximately 97.4% neon gas. Other excimer lasers having potential application in laser angioplasty include argon fluoride (ArF), xenon fluoride (XeF), and krypton chloride (KrCl).

The laser 40 comprises a laser discharge chamber 42 within which is mounted a first elongated electrode 44 and a second elongated electrode 46. Preferably, electrode 44 comprises multiple segments connected to a common bus 48, the entire assembly functioning as a single electrode. In one embodiment, the electrode 44 comprises approximately 68 individual segments 44a, 44b, 44c, ... 44n having a total discharge length of approximately 38 cm. Other embodiments may use a different number of segments to modify the performance specifications of the laser, e.g. output power, for different applications requirements. Each segment 44a, 44b, 44c, ... 44n is electrically connected to the common bus 48 by means of an inductive element 50a, 50b, 50c, ... 50n, respectively. In one embodiment, the inductance provided by each inductive element is approximately 150 nH. The second electrode 46 is mounted within the discharge chamber 42 so that the two electrodes 44 and 46, which are approximately 7 mm in width, are in substantial parallel alignment and separated by approximately 10 mm. In one embodiment, the electrode 46 is fabricated from a solid conductive material.

An optical axis 70 is formed between the laser electrodes 44 and 46 and within the discharge gap 52. A pair of windows 72 and 74 are mounted to the ends 76 and 78 respectively of the laser discharge chamber 42. The windows are mounted such that the optical axis 70 is intersected by the centers of the windows 72 and 74. Also mounted along the optical axis 70 are a high reflectance end mirror 80, a partially reflecting output mirror 82, a beam splitter 83 and a high reflectance 45 degree end mirror 84. In one embodiment, the beam splitter 83 comprises a 45 degree partially reflecting mirror. An output monitoring detector 86 is mounted adjacent the 45 degree partially reflecting mirror 83 so as to receive light reflected away from the optical axis 70. The region of space between the two mirrors 80, 82 is called the optical cavity of the laser. In one embodiment of the invention, the optical cavity is approximately 76 cm in length.

When a controlled electrical discharge is established between the first and second electrodes 44 and 46, atoms of the lasing medium are excited or pumped from their ground state energy level to higher energy levels or excited states. Excited atoms and molecules combine to form excited molecules. Many of these excited molecules will spontaneously return to their ground state energy level, thus emitting photons having energies equal to the energy difference between the energy of the decaying excited state and the energy of the ground state. This process is known as spontaneous emission. In the embodiment which utilizes KrF gas as the lasing medium, the wavelength of the emitted photons corresponding to the transition from the dominant excited state to the ground state is approximately 248 nm. The gaseous lasing medium between the electrodes is confined to the interior of the discharge chamber by the two windows 72 and 74. This arrangement protects the sensitive optical components such as the mirrors 80 and 82 from the highly corrosive environment of the gaseous lasing medium. In the embodiment utilizing KrF as the lasing medium, where the highly corrosive element fluorine is present in ionized form, the windows are preferably made from $MgF_2$, a material which is resistant to chemical attack by the ions in the lasing medium.

Photons emitted from the excited lasing medium in the direction of the optical axis 70 are reflected back and forth through the optical cavity by the mirrors 80 and 82. It is desireable to maximize the intensity of light within the optical cavity, therefore, end mirror 80 is preferably a high, nearly 100%, reflective mirror which will reflect nearly all of the incident photons back along the axis 70 and through the discharge gap 52. Output mirror 72 is partially reflective, thus allowing some fraction of the incident light to be transmitted through it and on toward the output of the device. In one embodiment, the output mirror 72 is approximately 80% reflective. In this embodiment, approximately 80% of the photons incident upon the mirror are reflected back along the optical axis to the end mirror 80 and are thus trapped within the optical cavity. The remaining approximately 20% of the photons are transmitted through the mirror 82 and thus escape from the optical cavity.

As the trapped photons propagate through the excited lasing medium in the discharge gap, they interact with other excited molecules of the lasing medium causing these molecules to prematurely decay and release additional photons of the same wavelength as the incident photons with which they interacted. This interaction is known as stimulated emission. Stimulated emission causes the intensity of light in the optical cavity to build to several orders of magnitude greater than the intensity of the original spontaneously emitted photons. The approximately 20% of this optical energy which escapes the optical cavity through the output mirror 82 is the useful output signal which may be directed by the articulating arm 30 and the fiber optic catheter 20 into a blood vessel to ablate plaque deposits within the lumen of the blood vessel.

The 20% of the optical energy which escapes the optical cavity through output mirror 82 is incident upon the beam splitter 83. In one embodiment, the beam splitter 83 comprises a 45 degree partially reflecting mirror. In this embodiment, the less than 4% of the light incident upon the mirror is reflected toward the output monitoring detector 86 while the remaining greater than 96% of the signal is transmitted to the 45 degree high reflectance end mirror 84. In one embodiment, the detector 86 comprises a photodiode. The photodiode detects the optical signals incident upon it and outputs an electrical signal which is proportional to the intensity of the incident optical signal. The electrical output is transmitted to the computer control system 41 where the value is compared to a reference value. If the value from the detector is different from the reference value, the computer system sends corrective signals to the high voltage power supply 64, or other components which are capable of changing the optical output of the laser. Thus, a feedback network comprising the detector 86, computer 41 and electrical components of the laser, maintains the output of the laser at a predetermined value.

High pressure, transverse discharges, such as those used to energize excimer lasers, are inherently unstable. As a consequence of this inherent instability, it is difficult to operate these lasers continuously. Therefore, excimer lasers are generally operated in a pulsed mode.

Pulsed operation is achieved by applying high voltage signals across the electrodes 44 and 46 in the form of pulses. The laser 40 is configured for pulsed mode operation by electrically connecting the output of a pulse forming network (PFN) 62 to the segmented electrode 44 via the bus 48. An input to the PFN is connected to a high voltage power supply 64. The high voltage power supply is coupled to a thyratron 66 which is also connected to an electronic trigger 68 and to the second electrode 46. In operation, the PFN 62 controls the size and shape of the high voltage from the supply 64. Upon receipt of a trigger signal from the trigger 68, the thyratron 66 functions as a switch for applying the high voltage pulse across the electrodes 44, 46. When the high voltage pulse appears across the electrodes, a gas discharge is created in the gas lasing medium. The discharge pumps the lasing medium into the excited state from which the stimulated laser emission described previously occurs. The output of optical laser energy occurs in pulses which are related to the high voltage pulses applied to the electrodes.

In the present invention, the KrF laser is operated with pulses having a width of approximately 75 nanoseconds at a pulse repetition rate of approximately 1000 pulses per second (1 kHz). Reliable attainment of these operating parameters is made possible in part by the inductors 50 and by two preionization electrodes 54a, 54b which are mounted adjacent the second electrode 46 (see FIG. 2).

Figure 2:
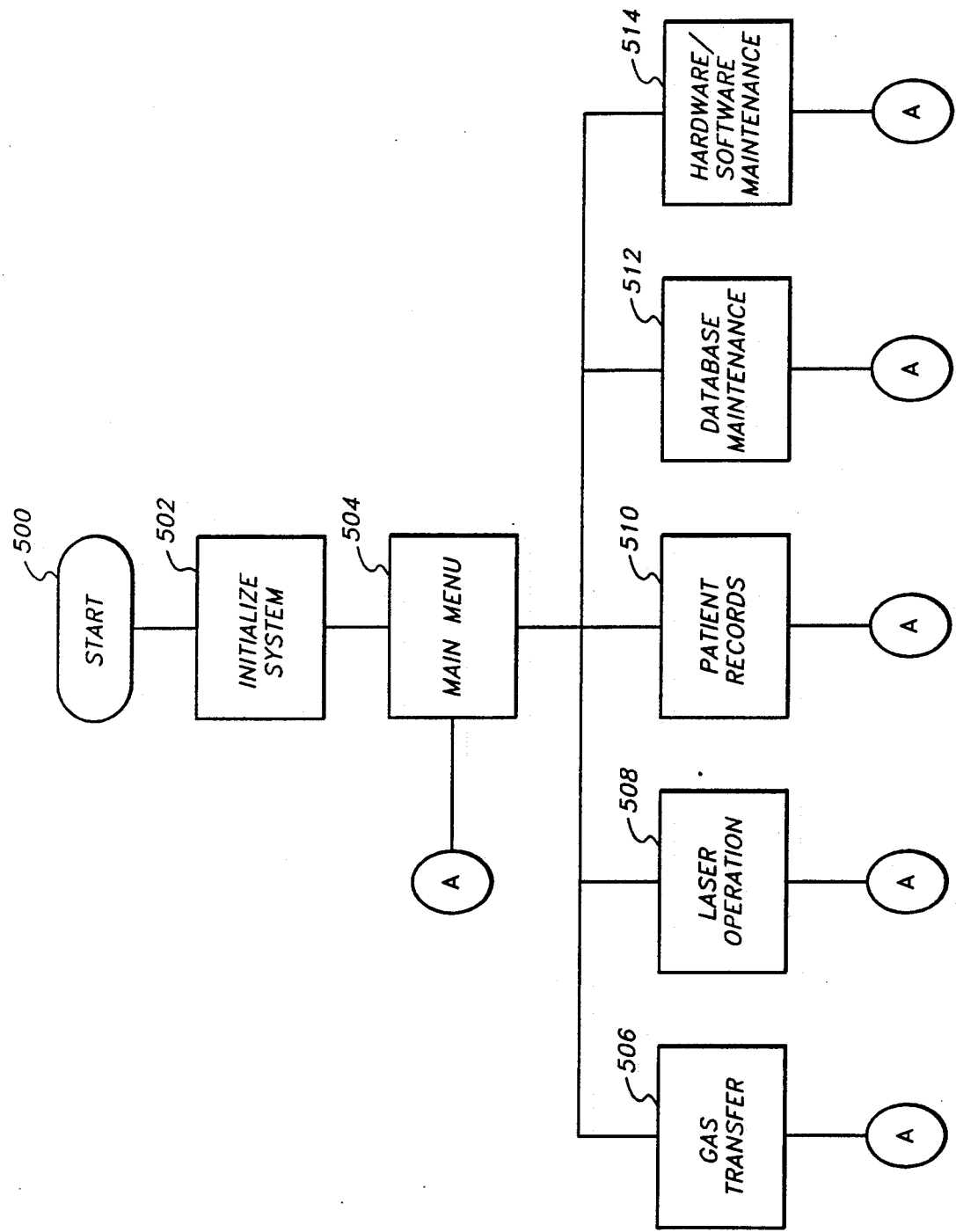
FIG. 2 is schematic illustration of the KrF excimer laser and associated electronics used in one embodiment of the invention.

In order to achieve stable laser action in these high pressure, transverse discharge, pulsed lasers, it is desireable that the discharge between the electrodes be uniform. One method of enhancing the uniformity of the discharge is to "preionize" (i.e., electrically precondition) the discharge volume. Preionization involves the creation of a uniform electron density exceeding about $10^7 \text{cm}^{-3}$ in the discharge volume just prior to the application of the main high voltage electrical discharge excitation pulse. The present invention utilizes a process known as corona preionization. One means of generating corona preionization in the laser 40 utilizes a three electrode system comprising the main electrodes 44 and 46 and one or more preionization electrode assemblies 54a and 54b. Each preionization electrode assembly, as illustrated in greater detail in the end view of the electrodes shown in FIG. 2, comprises a central conductor 56a, 56b, surrounded by a dielectric insulator 58a, 58b. The electrically insulated corona or preionization electrodes 54a and 54b are positioned on either side of either the first or second or both electrodes 44, 46. FIG. 2 illustrates a configuration where two preionization electrodes 54a and 54b are positioned adjacent to the second electrode 46, one preionization electrode on each side of the discharge portion of the electrode 46. The central conductor of the preionization electrodes is electrically connected to the electrode which is opposite the electrode to which it is adjacently positioned. For example, if the preionization electrode is positioned adjacent the electrode 46 as shown in FIGS. 1 and 2, then it will be electrically connected to the opposite electrode 44. Alternatively, if the preionization electrode were positioned adjacent the electrode 44 (not shown), then they would be electrically connected to the opposite electrode 46.

The corona preionization system is activated by the application of a pulsed voltage between the two main discharge electrodes 44, 46. This pulse is supplied to the main discharge electrodes by the pulse forming network (PFN) 62 as previously described. Since the preionization electrode 54 is electrically connected to the segmented electrode 44, the same voltage which is generated between the main electrodes 44, 46 also appears between the central conductor 56 and the main electrode 46. Since the central conductor 56 is positioned extremely close to the electrode 46, a very high electric field gradient is established which creates a corona discharge. The current in the corona discharge is limited to displacement current because of the intervening dielectric insulator 58 which surrounds the central conductor 56. This corona discharge preionizes the gas in the main discharge gap 52, making the main laser discharge more uniform and stable. In the embodiment disclosed above, only two preionization electrodes have been used, however, it may be desireable to use four preionization electrodes. In addition to the two preionization electrodes located adjacent the electrode 46, two additional preionization electrodes may be located adjacent the main discharge electrode 44. Alternatively, if the separation between the main laser discharge electrodes is small, use of a single preionization electrode may be sufficient.

Another phenomena which often leads to instability in pulsed high pressure transverse discharge lasers is the formation of streamer arcs between the main electrodes. In rare gas halide gas mixtures, such as KrF, the degree of stability is measured by the energy loading and stable discharge time. In general, as the rate of energy deposition into the gaseous medium increases, streamer arcs between the main electrodes are observed throughout the discharge. This results in a limited lasing time since the useful energy deposition time is limited by the time it takes for the streamer arcs to propagate across the discharge gap.

The present invention utilizes two features which help stabilize the laser by inhibiting formation of streamer arcs between the electrodes. First, the use of a segmented electrode is advantageous because it localizes catastrophic breakdowns to small regions of the discharge. That is, the formation of a streamer arc at one segment of the electrode does not affect the voltage of the entire electrode and hence the discharge characteristics at other regions of the electrode are not perturbed as much as they would be if the main electrode were a single electrical unit. A second feature, inductive stabilization of each segment of the electrode, also helps to inhibit the formation and growth of streamer arcs. Inductive stabilization is a commonly used technique for quenching and preventing formation of streamer arcs in gaseous discharges. Formation of streamer arcs is preceded by an instability in the discharge region in the vicinity of the arc. This discharge instability is accompanied by a rapid increase in the current at that location. The individual inductors 50a, 50b, 50c, . . . , 50n attached to each segment 44a, 44b, 44c, . . . , 44n, respectively, limit the rate at which electric current can pass through the individual inductive elements. The rapid increase in current causes a voltage drop across the inductor given by $v = L di/dt$ where L is the inductance of the inductor and $di/dt$ is the time rate of change of current through the inductor. This voltage drop across the inductor causes a corresponding decrease in voltage across the discharge gap which quenches the formation of the streamer arc.

Thus, the combination of preionization electrodes, a segmented electrode and inductive stabilization of each segment, results in a laser which is extremely stable over extended periods of time. One characteristic of stabilization is an extended pulse width. Since the peak power of a laser is defined as the energy of the pulse divided by the pulse duration, this characteristic enables the laser to deliver high energy pulses having reduced peak power. As previously described, this is advantageous since it is the high peak power of a pulse which damages the fiber optics and other components in the optical path of the pulse. Therefore, a laser having long pulses can deliver the same average power over extended periods as a laser having shorter duration pulses without causing substantial damage to the optical components of the system.

Other features of the laser 40 which contribute to its extended performance time include a means for circulating the lasing gas mixture within the chamber 42, a means for cooling the gas mixture in the chamber and a means for removing impurities contained in the gas while the laser is operating.

As shown in FIG. 1, the gas circulating means comprises a circulating blower 88 which is mounted within the laser discharge chamber 42. The blower is driven by a motor 89 located external to the chamber. The flow of gas within the interior of the discharge chamber created by the blower is controlled by baffles 90. The baffles are arranged so that the circulating gas within the chamber passes over a heat exchanger 92 to remove heat from the circulating gas.

Impurities, which are created in the lasing gas mixture by the electrical discharge, are removed by a cryogenic trap 94. The gas in the chamber is circulated by means of a pump 93 through the cryogenic trap 94 for removal of any impurities created in the discharge.

As described, the operational lifetime of the laser 40 is extended by virtue of the large gas volume provided by the chamber 42, the circulating blower 88, the heat exchanger 92 and the cryogenic trap 94. All of these components contribute to extended operation times by continuous treatment of the lasing medium to remove heat and impurities generated in the discharge. At the same time, these features are integral parts of the laser which are all sealed into a single sealed system to reduce the probability of any toxic components of the gas lasing medium from escaping and creating a personnel hazard. The integrity of this gas handling system is constantly monitored by a fluorine gas detector 95 located near the chamber 40. If any leaks were to develop in the gas handling system, the detector would sense the fluorine gas and sound an alarm.

Periodically, the lasing medium gas in the chamber becomes contaminated, thus degrading the performance of the laser. When this occurs, it is desireable to empty the gas from the chamber, purge any remaining contaminates and replace the lasing medium gas with a fresh supply. Since there is a higher probability that leaks will occur during this process, it is desireable to perform this activity in a location which is remote from the operating room or other areas of the hospital where leaks could result in a personnel hazard. Accordingly, in one embodiment of the laser 40, a gas transfer system 98 is used to recharge the laser with a fresh supply of lasing medium gas. The gas transfer system is preferably a completely separate unit from laser 40 thus enabling the transfer system to be located in a remote area where the transfer of gas between the laser and the transfer system can be performed without endangering personnel. Once the lasing medium gas has been replaced at a safe location, the laser can be resealed, checked for leaks and returned to the operating room for additional use. Continued monitoring for leaks is provided by the detector 95 as previously described.

Further discussion of multisegmented inductor stabilized excimer lasers and other features of pulsed lasers in general may be found in the following references: U.S. Pat. No. 4,240,044 entitled "PULSED LASER ELECTRODE ASSEMBLY"; U.S. Pat. No. 4,601,039 entitled "INDUCTIVELY STABILIZED, LONG PULSE DURATION TRANSVERSE DISCHARGE APPARATUS"; U.S. Pat. No. 4,143,337 entitled "METHOD OF PUMPING"; U.S. Pat. No. 3,408,593 entitled "SCANNED LASER BEAM DEVICE"; Great Britain Patent No. 1,348,613 entitled "PULSED GAS LASER"; Canada Patent No. 897,754 entitled "MOLECULAR GAS LASER ENERGIZED BY DOUBLE DISCHARGE"; "MINI-LASERS FOR HIGH-REPETITION-RATE RARE GAS HALIDE OSCILLATORS", SPIE Vol. 190, LASL Optics Conference (1979), pp305-310; "EXPERIMENTAL STUDIES OF A KRF AND ARF DISCHARGE LASER", IEEE Journal of Quantum Electronics, Vol. QE-14, No. 12, December 1978, pp. 944-950; "A TRANSVERSE EXCITED MULTIATMOSPHERE $CO_2$ WAVEGUIDE LASER", Applied Physics Letters, Vol. 31, No. 3, August 1977, pp. 176-178; "A STUDY OF EXCIMER LASER PREIONIZATION TECHNIQUES", Topical Meeting on Excimer Lasers held Sept. 11-13, 1979 in Charleston, S.C., pp.WB4-1-WB4-3; "A RESISTIVELY STABILIZED XeCl LASER OPERATING AT 200 Hz", IEEE Journal of Quantum Electronics, Vol. QE-17, No. 8, August 1981, pp.1315-1317; and "INDUCTIVELY STABILIZED RARE-GAS HALIDE MINILASER FOR LONG-PULSED OPERATION, J. Appl. Phys., 54(3), March 1983, pp. 1224-1227.

ARTICULATING ARM

The output of the laser 40 is directed by the mirror 84 toward the input shutter 32 of the articulating arm 30. The shutter is controlled by the computer 41 depending upon which desired conditions must be satisfied before the optical energy is permitted to enter the arm. For example, in one embodiment, the desired conditions include the requirement that the laser catheter 20 be attached to the arm. This is monitored by the output interlock 34 at the output of the arm. If the signal from the interlock to the computer indicates that the catheter is correctly positioned, then the computer sends a signal to the input shutter 32 which opens the shutter and permits the laser light to enter the arm and hence the catheter.

In one embodiment, shown in FIG. 1, the articulating arm 30 comprises the input shutter 32, a first mirror 100, a first rotational joint 110, a focusing lens 106, a second rotational joint 120, and the output interlock 34. These components are positioned along and aligned with an optical path 126 along which light which enters the arm at shutter 32 travels. The light travels along the path 126 through the arm until it exits the arm at the interlock 34. The lengths of the optical path segments 126a, 126b, 126c, and 126d which connect the above components of the arm may be chosen as desired for specific application requirements.

The rotational joints 110, 120 further comprise reflection assemblies 130 which articulate with the motion of the joints such that optical signals entering the joints along the optical path 126 exit the joints substantially along the same optical path 126. In one embodiment, where the joints are free to rotate about two orthogonal axes, the reflection assemblies 130 comprise two mutually perpendicular mirrors which are oriented at 45 degrees with respect to the optical axis 126. These types of mechanisms are commonly used in the field of optics and will not be further described herein.

The lens 106 focuses the light propagating along the optical path 126. In one embodiment, the lens 106 is adjusted so that a focal point is formed along the axis segment 126d at a location near, but not coincident with, the input end 22 of the fiber optic catheter. This is a technique commonly used for injecting energetic laser light signals into optical fibers. It is advantageous because it reduces the energy density per unit of area at the face of the fiber and thus reduces damage to the input face of the fiber caused by intense optical signals.

Figure 1B:
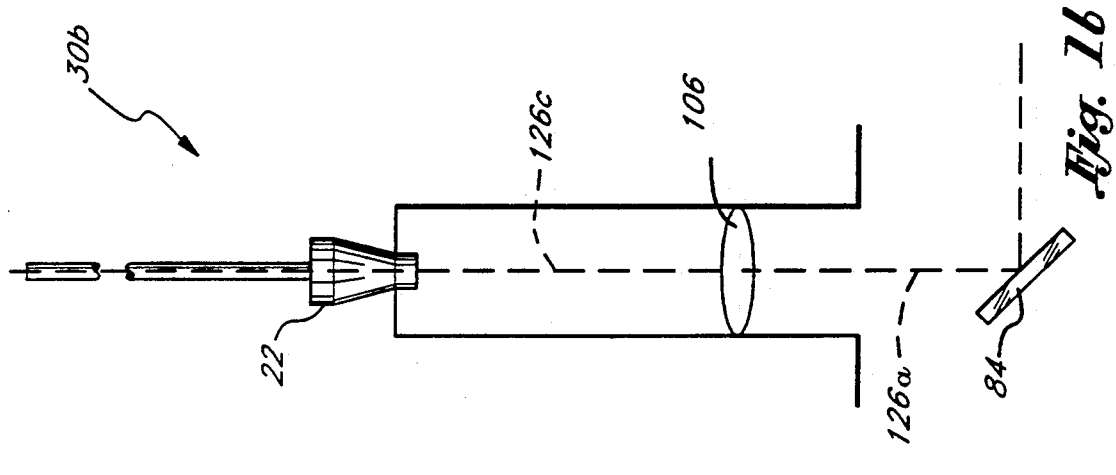
FIG. 1b is an illustration of another embodiment of the articulating arm used to transport the laser light from the laser to the fiber.
Figure 1A:
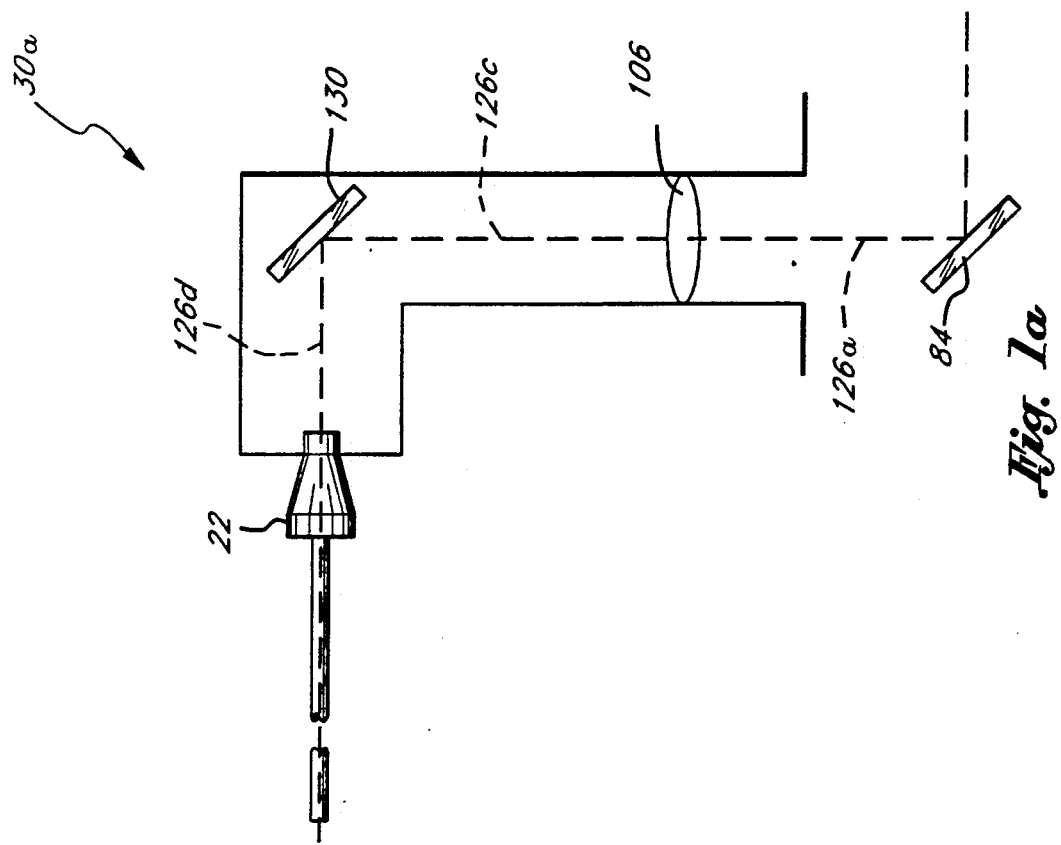
FIG. 1a is an illustration of one embodiment of the articulating arm used to transport the laser light from the laser to the fiber.

Two alternate embodiments for articulating arms are shown in FIGS. 1a and 1b. FIG. 1a shows an articulating arm 30a comprising the focusing lens 106 and the mirror 130. These components are positioned along and aligned with optical path 126a along which light may enter the arm. The light travels along the path 126a through lens 106, then along path 126c until it is reflected by mirror 130 onto path 126d, whereupon it enters the fiber at the input connector 22. The lengths of the optical path segments 126a, 126c, and 126d which connect the above components of the arm may be chosen as desired for specific application requirements. As previously described, the mirror 130 may also comprise a rotational optical joint.

FIG. 1b shows an articulating arm 30b comprising the focusing lens 106. The lens is positioned along and aligned with optical path 126a along which light may enter the arm. The light travels along the path 126a through lens 106, then along path 126c whereupon it enters the fiber at the input connector 22. The lengths of the optical path segments 126a and 126c may be chosen as desired for specific application requirements.

FIBER OPTIC CATHETER

The catheter 20 is positioned to receive light from the articulating arm 30. FIGS. 3a and 3b show detailed drawings of one embodiment of the catheter. The input connector 22 is connected to a first catheter tube 202 via a stress relief 208. In the embodiment shown, there are two service ports 212 and 216 connected to the catheter tube 202 via manifolds 220 and 224 respectively. The second catheter tube 228 is attached to the last downstream manifold 220 via a second stress relief 232. A length of flexible fiber optic 236 is contained within the catheter tubes 202 and 228 and extends from the input of the connector 22 to the end 240 of the catheter. An exploded view of the end 240 of the catheter 20 is shown in FIG. 3b. A first radiopaque marker 244 is attached to the end of the fiber 236. A second radiopaque marker 248 is attached to the end of the catheter tube 228. The radiopaque markers 244 and 248 may be made of any material which will be visible in an X-ray of an artery into which the catheter is inserted. For example, the markers may comprise thin layers of lead or other metallic materials.

The catheter tubes 202 and 228 function as guides for the fiber 236. First, the catheter tube 228 is introduced percutaneously into the artery and advanced to the site of obstruction using fluoroscopic guidance to follow the position of the radiopaque marker 248. The optical fiber 236 is then inserted through the catheter and positioned at the lesion again using fluoroscopic guidance to follow the position of the radiopaque marker 244. Once in position, laser energy from the laser 40 is permitted to enter the fiber 236 at the input end 22 and be carried through the fiber to its distal end 240. When the laser energy exits the distal end and is absorbed by the target plaque, the plaque is ablated as previously described. In a preferred embodiment, the energy density of the 248 nm or 308 nm (nanometer) light propagating through the fiber is at least on the order of about 100–200 mJ/cm$^2$ (millijoules per square centimeter). In general, shorter ultraviolet (U.V.) wavelengths have a higher ablation efficiency than longer U.V. wavelengths, and thus, the appropriate energy density depends in part on the wavelength of the light. For example, at 308 nm, the energy density might be on the order of several hundred to over a thousand mJ/cm$^2$. The duration of each pulse in not critical but is preferably on the order of at least a few tens of nanoseconds.

The input ports 212 and 216 enable perfusates such as saline, fluorocarbons, diluted blood or radiopaque dyes to be delivered into the artery at the end 240 of the catheter.

Structural details of a typical optical fiber 236 are shown in the section view of FIG. 4. The fiber 236 comprises a core 300, a cladding 310, and an outer protective jacket 320. In one embodiment, the core has a diameter of approximately 400 μm, the core plus cladding diameter is approximately 440 μm and the jacket diameter is approximately 650 μm. In another embodiment, the core has a diameter of approximately 800 μm, the core plus cladding diameter is approximately 880 μm and the jacket diameter is approximately 1,250 μm.

FIG. 5a illustrates a cross section view of a typical optical fiber having a core 300 and a cladding 310. The core 300 is shown as having a radius $r_1$ and the cladding 310 having a radius $r_2$. FIG. 5b illustrates the index of refraction profile for a typical step index optical fiber. The core is shown as having a constant index of refraction of magnitude $n_1$ over its entire diameter and the cladding as having an index of refraction of magnitude $n_2$ which is likewise constant over the entire cross section of the cladding. If the angle of incidence of the light upon the interface between the core and the cladding is less than the critical angle of total reflection, then light propagating in the core will be reflected back into the core at the interface. This critical angle is determined by the ratio of the two indices of refraction $n_1$, $n_2$ of the core and the cladding, respectively. Light is strongly confined to the core when the core index $n_1$ is greater in value than the cladding index $n_2$. Therefore, most common optical fibers have the configuration of the fiber illustrated in FIG. 5b.

In some specialized applications of optical fiber, it has been found advantageous to use a core which has an index of refraction which varies as the radius of the core. Such a fiber is commonly referred to as a graded index fiber. A plot of the core and cladding indices of refraction for a typical graded index fiber is shown in FIG. 5c. The most common application for graded index fibers is in the optical communications industry where it is important to preserve phase coherence of light pulses propagating through the fiber.

Both the stepped index fibers and the graded index fibers, when used to transmit energetic optical signals often exhibit very low damage thresholds. Specifically, when these fibers are used to transmit the 248 nm wavelength light produced by the KrF laser of the present invention, the useful lifetime of the fiber is measured in minutes. This makes it difficult to perform certain laser angioplasty procedures which may require use of the fiber for a few hours. Further discussion of the transmission characteristics of optical fibers may be found in the following references: "ALTERATION OF THE TRANSMISSION CHARACTERISTICS OF FUSED SILICA OPTICAL FIBERS BY PULSED ULTRAVIOLET RADIATION", SPIE Vol. 540, Southwest Conference on Optics (1985) and "PULSED LASER DAMAGE TO OPTICAL FIBERS", Applied Physics, Vol. 24, No. 19, October 1985.

The optical fiber shown in FIG. 5d has been found to exhibit a useful life for transmission of the ultraviolet light from the KrF laser which is superior to most, if not all, commercially available step index or graded core index fibers. The fiber in FIG. 5d comprises a core which has a constant index of refraction $n_5$ throughout its entire diameter, similar to the step index fiber of FIG. 5b. However, the fiber also comprises a cladding which has a variable index of refraction. As shown in FIG. 5d, the index of refraction of the cladding at the interface between the core and cladding is approximately $n_5$ and gradually decreases as the radius of the cladding increases until it reaches a value $n_6$ at the outer radius of the cladding.

The theoretical explanation for the superior UV transmission properties of the graded-index cladding fiber is not well understood at the present time. However, the property has been demonstrated empirically. A manufacturer of a graded-index cladding fiber, identified as Type ST400E, is Mitsubishi Cable Industries Ltd. of Japan. A U.S. distributor of this fiber is Mitsubishi Cable America, Inc. in New York, N.Y.

One fiber optic catheter assembly which may be used in the present invention is disclosed in U.S. Pat. No. 4,681,104, entitled "APPARATUS FOR FOCUSING AN INTRAVASCULAR LASER CATHETER". The information contained in this patent is hereby incorporated herein by reference.

COMPUTER CONTROL SYSTEM

Figure 6:
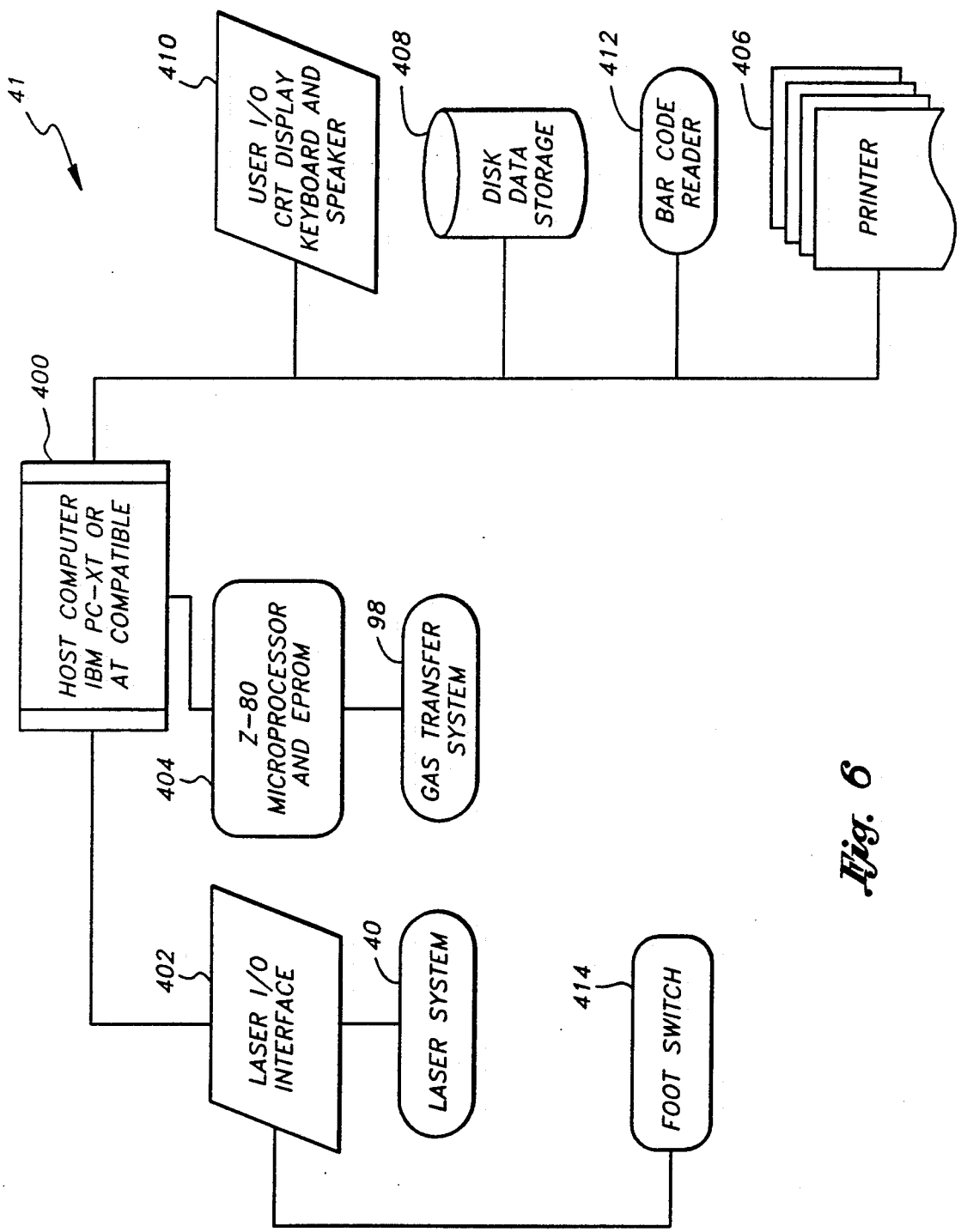
FIG. 6 is a block diagram of the computer control system hardware.

A block diagram of the computer control system 41 used in one embodiment of the invention is shown in FIG. 6. The illustrated system comprises a host computer 400, a laser interface card 402, a gas transfer control microprocessor 404, and assorted input/output (I/O) peripheral devices including a printer 406, a disk storage system 408, a video display terminal/keyboard/speaker 410, a bar code reader 412 and a foot operated switch 414. The host computer 400 is preferably an IBM, or compatible, PC-XT or AT. One such computer which may be used is a "Gridcase Model EXP 3", available from Grid Computer in Fremont, Calif. One skilled in the art will recognize that other types of computers and microprocessors could also be used.

The laser interface card 402 is plugged into the bus of the computer 400 and provides a hardware link between the computer 400 and the laser hardware 40. The foot switch 414 is connected to the card 402 and is used to trigger output pulses from the laser. The interface card 402 performs many functions which, in general, include communications between the computer 400 and the laser 40. Additionally, the card 402 monitors the status of numerous operations parameters of the laser system including safety interlocks, water flow, water temperature, gas pressure, electrical signals, etc.. These parameters are sensed and measured utilizing standard transducers, well known to those skilled in the art of computer or microprocessor control of electro-mechanical systems.

In one embodiment, the gas transfer control microprocessor 404 comprises a Z-80 microprocessor with a software program for control of the gas transfer system being stored in an erasable-programmable-read-only-memory (EPROM). Since the Z-80 is capable of stand alone operation, the gas transfer system can be controlled either by the main computer 400 or by an auxiliary maintenance computer. This enables the gas system to be monitored and controlled by computer 400 during operation of the laser angioplasty system of the present invention. As described previously, it is often desireable to perform certain maintenance procedures on the gas handling system in a remote location. Since the Z-80 can be connected to a maintenance computer, separate from the main computer 400, the entire gas transfer system can be placed in a remote location for test and maintenance without compromising the computer directed monitoring and control functions of the system.

The user I/O, which comprises a cathode ray tube (CRT) video display, or equivalent, a keyboard and audio speaker, provides for communication with the computer, and hence the entire laser angioplasty system, by the human operator of the system. The communications may be by any of the well known means, including keyboard, screen displayed menus, etc. In one embodiment of the present invention, the human link is provided by a menu driven system, augmented by the bar code reader 412 and keyboard. The bar code reader may be used to read and input to the computer various kinds of data including patient identification data from a patient's hospital entrance bracelet, and the serial numbers from the appliances used to perform the medical procedures on the patient, for example, the laser catheter. Bulk storage of data is provided by the disk storage system 408 and hardcopy output from the computer is provided by the printer 406.

In one embodiment of the present invention, the interface between the computer and the system operator is provided via a menu driven system. A typical menu system is shown in FIG. 7. The program starts in a block 500 and proceeds to an initialization task represented by block 502. Generally, the initialization is performed on start up of the system or at periodic intervals. After initialization of the system, the program proceeds to the main menu represented by block 504. From the main menu, submenus for specific procedures can be selected. Submenus shown in FIG. 7 include Gas Transfer 506, Laser Operation 508, Patient Records 510, Database Maintenance 512 and Hardware/Software Maintenance One skilled in the art will recognize that other submenus can be added as desired. Upon completion of the tasks of a particular submenu, control is returned to the main menu, as indicated by the transfer blocks labelled "A".

Figure 8:
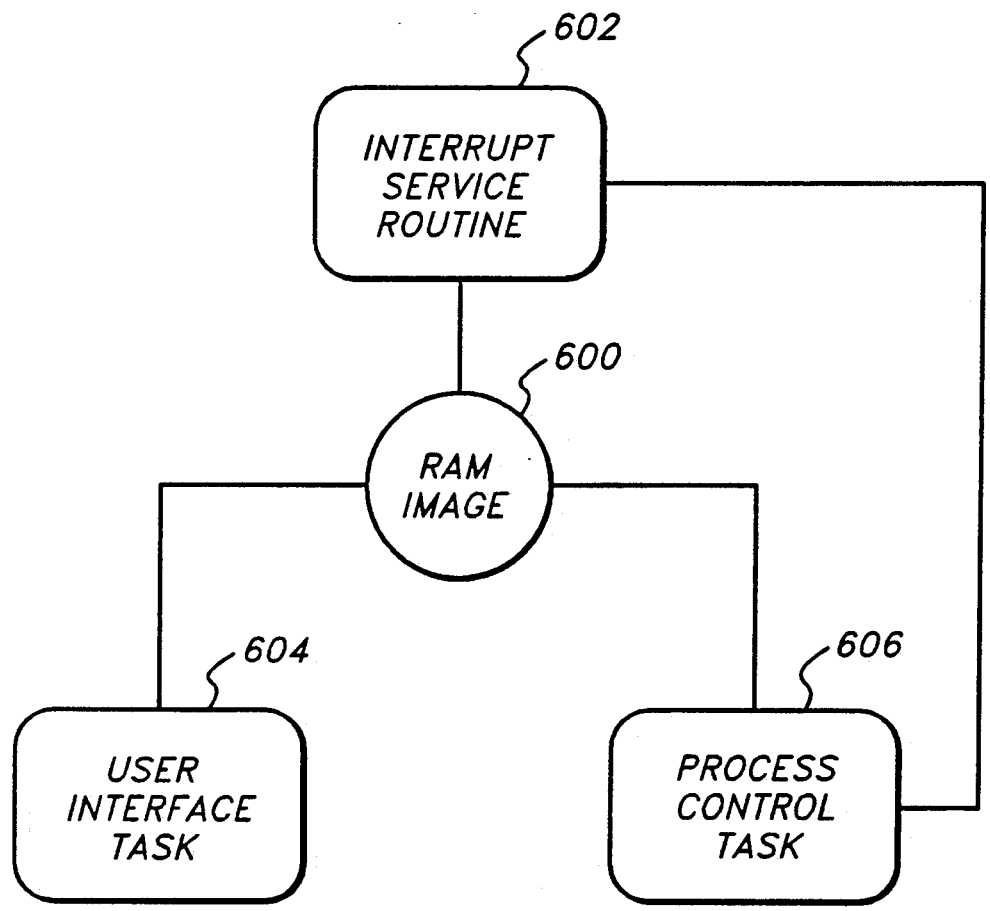
FIG. 8 is a block diagram illustrating the hierarchy of the various portions of the software program.

Efficiency of the main computer 400 is enhanced by operating under a MULTIDOS operating system, such as that available from Anex Technology Inc., in Congers, N.Y. This enables various portions of the laser angioplasty system to have access to the Random Access Memory (RAM) of the main computer, via software tasks, according to a predetermined assignment of task priorities. In one embodiment of the present invention, as shown schematically in FIG. 8, access to the main computer RAM image 600, is provided through three different software tasks, an Interrupt Service Routine (ISR) 602, a User Interface Task (UIT) 604, and a Process Control Task (PCT) 606. The UIT runs in the foreground and the ISR and PCT run in the background of the computer operating system.

Typical foreground tasks run by the User Interrupt Task (UIT) 604 include: creation of system state information for the shared RAM image, creation of timer information to turn the laser ON/OFF, output to all lines of the CRT except the last two lines, receive input information from the bar code reader, receive input information from the keyboard, creation of output signals for the speaker to generate audible sounds, read and write to the database, output information to the printer and input/output information to/from the disk drive. The data base includes patient information, product information, treatment information, maintenance logs and error logs.

The Process Control Task (PCT) 606 defines and controls the background operations in the computer system 400. The most important task performed by the PCT is the operation of the Interrupt Service Routine (ISR) 602. Typical tasks performed by the ISR include: operation of a process loop, maintenance of a sensor and transition interpretation map, translation of time critical sensor and control validation data, real time system enable/disable (e.g. foot switch enable and faults disable), and setting of clock rate at 72.8 Hz or other desired rate. The gas transfer Z-80 microprocessor control system links to the main computer via an RS-232 line which is monitored and serviced by the ISR.

Other tasks performed by the PCT include: set up control and validation maps for the ISR to minimize ISR execution overhead, creation of fault and warning messages for delivery to the UIT, creation of digital control output signals, creation of error and maintenance logs, creation of system status information, creation of fault masks, creation of messages for the last two lines of the CRT, creation of signals to generate speaker sounds, and creation of system watch dog status updates.

The system and process described herein were developed primarily for delivery of high energy laser light to blockages in arteries for performance of laser angioplasty procedures. However, it may also be useful in other situations where delivery of high intensity UV laser light to a remote location is desired.

While the above description comprises one preferred embodiment of the invention as applied to laser angioplasty, there are other embodiments which will be obvious to those skilled in the art. Additionally, one skilled in the art will readily appreciate that the versatility and adaptability of the system makes it useful for numerous applications of delivery of energetic laser light signals.

The invention may be embodied in other specific forms without departing from its spirit or essential characteristics. The described embodiments are to be considered in all respects only illustrative and not restrictive. The scope of the invention is, therefore, indicated by the appended claims rather than by the foregoing description. All changes which come within the meaning and range of equivalency of the claims are to be embraced within their scope.

We claim:

1. An apparatus for producing and transmitting energetic optical signals, comprising:
an excimer laser for producing ultraviolet light, said laser comprising:
(a) a first elongated laser electrode having a plurality of segments, there being associated with each of said segments an individual inductive element through which each said segment is connected to a common bus;
(b) a second elongated laser electrode spaced apart from said first laser electrode, said second electrode positioned substantially parallel to said first laser electrode and substantially coextensive therewith, the space between said first and second laser electrodes forming a laser discharge gap;
(c) a preionizer positioned adjacent to one of said first and second laser electrodes throughout the effective length of said one laser electrode, said preionizer comprising a conductive element within ar insulting tube, said insulating tube proximate said one laser electrode and said conductor element in electrical connection with the other of said laser electrodes;
(d) a housing for said first and second laser electrodes, said housing defining a cavity suitable for confining a gaseous laser medium, said housing cavity allowing exchange of said gaseous laser medium between said cavity and said laser discharge gap;
(e) a pulse forming network for producing electrical pulses for application to said laser electrodes to generate an electrical discharge in said gaseous laser medium in said laser discharge gap;
(f) a gas circulator for circulating said laser medium within said housing cavity; and
(g) a trap through which said gaseous laser medium may be passed, said trap removing impurities from said gaseous medium; an optical fiber having an input end and an output end, said input end receiving optical signals from said laser and guiding them through said fiber to said output end, said fiber further comprising a substantially rod shaped core material surrounded by a substantially tube shaped cladding material, said cladding material having an optical index of refraction which is less than or equal to the index of refraction of said core material at an interface between the core and the cladding, the index of refraction of the cladding material decreasing as the radial distance from said interface increases; and
a control system for monitoring and controlling the operation of said laser.

2. The apparatus of claim 1, wherein said gaseous laser medium comprises krypton and fluorine.

3. The apparatus of claim 1, wherein said gaseous laser medium comprises xenon and chlorine.

4. The apparatus of claim 1, further comprising a catheter for guiding said optical fiber to a remote location.

5. The apparatus of claim 1, further comprising a fluorine detector.

6. The apparatus of claim 1, wherein said control system further comprises a computer control system.

7. The apparatus of claim 1, wherein said ultraviolet light has a wavelength on the order of about 250 nm.

8. The apparatus of claim 1, wherein said ultraviolet light has a wavelength on the order of about 310 nm.

9. The apparatus of claim 1, wherein said ultraviolet light has a wavelength which is selected to nonthermally ablate biotic material.

10. The apparatus of claim 1, wherein said optical signals from said laser are in the form of pulses.

11. The apparatus of claim 10, wherein said pulses have a duration on the order of approximately 75 ns.

12. The apparatus of claim 10, wherein said pulses are at a frequency of on the order of about 1,000 pulses/second or less.

13. The apparatus of claim 1, wherein said optical signals comprise a series of pulses, each of said pulses having a duration of at least a few tens of nanoseconds.

14. The apparatus of claim 1, wherein said optical signals comprise a series of pulses, each of said pulses having an energy density on the order of at least about 100 millijoules/cm$^2$, and having a duration of at least a few tens of nanoseconds.

15. The apparatus of claim 1, wherein said optical signals comprise a series of pulses, each of said pulses having an energy density of at least several hundred millijoules/cm$^2$ and having a duration of at least a few tens of nanoseconds.

* * * * *